United States Patent [19]

Suganuma et al.

[11] Patent Number: 4,576,816

[45] Date of Patent: * Mar. 18, 1986

[54] DENTIFRICE COMPOSITION

[75] Inventors: Nobuo Suganuma, Funabashi; Masafumi Anzai, Kawasaki; Nobuyuki Takada, Chigasaki; Hiromichi Ichikawa, Mitaka, all of Japan

[73] Assignee: Lion Corporation, Tokyo, Japan

[*] Notice: The portion of the term of this patent subsequent to Dec. 3, 2002 has been disclaimed.

[21] Appl. No.: 407,901

[22] Filed: Aug. 13, 1982

Related U.S. Application Data

[63] Continuation of Ser. No. 190,175, Sep. 23, 1980.

[30] Foreign Application Priority Data

Oct. 27, 1979 [JP] Japan .................. 54-139057

[51] Int. Cl.$^4$ .................. A61K 7/18; A61K 7/20
[52] U.S. Cl. .................. 424/50; 424/49; 424/52
[58] Field of Search .................. 424/49, 50, 52

[56] References Cited

U.S. PATENT DOCUMENTS

| | | |
|---|---|---|
| 2,010,910 | 8/1935 | Atkins . |
| 2,550,207 | 4/1951 | Tainter et al. . |
| 2,818,371 | 12/1957 | Wessinger . |
| 3,060,098 | 10/1962 | Gershon . |
| 3,329,564 | 7/1967 | Aguiar et al. . |
| 3,622,661 | 11/1971 | King et al. . |
| 4,098,878 | 7/1978 | Baines et al. . |
| 4,118,471 | 10/1978 | Pensak . |
| 4,123,517 | 10/1978 | Baines et al. . |
| 4,150,113 | 4/1979 | Hoogendoorn et al. . |
| 4,168,301 | 9/1979 | Pugh et al. . |
| 4,269,822 | 5/1981 | Pellico et al. . |

FOREIGN PATENT DOCUMENTS

| | | |
|---|---|---|
| 1948469 | 4/1971 | Fed. Rep. of Germany . |
| 52-54037 | 5/1977 | Japan . |
| 1197164 | 7/1970 | United Kingdom . |
| 1296952 | 11/1972 | United Kingdom . |
| 1373003 | 11/1974 | United Kingdom . |

OTHER PUBLICATIONS

CPC International, Inc., Res. Dsicl., 1980, 193:195-7, Method Using Glucoamycase Immobilized on Porous Alumina, Chem. Abstracts, 93:9878v (1980).

*Primary Examiner*—Shep K. Rose
*Attorney, Agent, or Firm*—Birch, Stewart, Kolasch & Birch

[57] ABSTRACT

A dentifrice composition is disclosed which comprises 100–100,000 units per gram of the composition of dextranase and 20–90% by weight of the composition of an aluminum oxide compound having the formula:

$$Al_2O_3 \cdot nH_2O$$

wherein $n \geq 0$, with an average particle size of 1–50 microns as a main abrasive. Dextranase is maintained stable in the dentifrice composition and the composition itself is stable, subject to minimal aging discoloration.

15 Claims, No Drawings

DENTIFRICE COMPOSITION

This application is a continuation of copending application Ser. No. 190,175, filed on Sept. 23, 1980.

BACKGROUND OF THE INVENTION

This invention relates to dentifrice compositions containing dextranase. Such dentifrice compositions may be used in the form of toothpastes, toothpowders and the like.

It is well known, for example, from U.S. Pat. No. 3686393 to incorporate dextranase in dentifrice compositions as an active ingredient for caries prophylaxis to prevent the formation of dental plaque.

Inconveniently, dextranase tends to be deactivated by moisture, anionic surfactants and other ingredients in dentifrice compositions. Several approaches have been proposed to stabilize dextranase, for example, blending a flavor such as terpene hydrocarbons, aliphatic alcohols, etc. as disclosed in Japanese Pat. No. 802,787 or by blending gelatin as disclosed in U.S. Pat. No. 3,981,989 and G.B. Pat. No. 1,427,300. Other proposals are disclosed in U.S. Pat. Nos. 3,991,177, 4,115,546 and 4,140,750.

Such stabilization, however, is not sufficient particularly when dentifrice compositions are stored at elevated temperatures. There therefore is a need for more effectively stabilizing dextranase as well as enhancing the stability of a dextranase-containing dentifrice itself.

SUMMARY OF THE INVENTION

Therefore, an object of this invention is to provide a dentifrice composition in which dextranase is maintained stable.

Another object of this invention is to provide a dextranase-containing dentifrice composition which is highly stable and subject to minimal discoloration during storage.

According to the present invention, there is provided a dentifrice composition comprising 100–100,000 units per gram of the composition of dextranase and 20–90% by weight of the composition of an aluminum oxide compound having the formula:

$$Al_2O_3 \cdot nH_2O \qquad (1)$$

wherein $n \geq 0$, with an average particle size of 1–50 microns as a main abrasive.

Dextranase is highly stable and maintained at a sufficient concentration in the dentifrice composition of this invention even after extended storage as the result that the aluminum oxide compound of formula (1) is used as a main abrasive. Additional advantages are also found in that the dentifrice composition itself is stable, subject to minimal aging discoloration, and effective to clean the tooth.

The above and other objects, features and advantages of this invention will become more apparent and understandable from the following Detailed Description, Examples and Claims.

DETAILED DESCRIPTION OF THE INVENTION

The dentifrice composition of this invention comprises dextranase as an active ingredient and the above-defined aluminum oxide compound as a main abrasive.

The amount of dextranase blended is generally 100–100,000 units per gram of the composition, preferably 1,000–50,000 units per gram of the composition. One unit of dextranase indicates the productivity of reducing sugars corresponding to 1 $\mu$g of glucose/min. when dextranase is incubated with substrate of dextran.

The aluminum oxide compounds represented by the general formula:

$$Al_2O_3 \cdot nH_2O \qquad (1)$$

wherein $n \geq 0$, preferably $3 \geq n-0$, include aluminum oxide when $n=0$ (that is, an aluminum compound having no water of crystallization and represented by $Al_2O_3$, to be referred to as "alumina", hereinafter) and hydrated aluminum oxides when $n>0$ (that is, aluminum compounds having water of crystallization, to be referred to as "hydrated aluminas", hereinafter).

Many types of aluminas and hydrated aluminas are known including $\alpha$, $\gamma$, $\delta$, $\eta$, $\theta$, $\kappa$, $x$, $\rho$ and $\beta$ types classified in terms of crystal systems and physical properties. Among them, $\alpha$-alumina and hydrated $\alpha$-alumina are preferred because of high stability.

The hydrated aluminas which can be used herein are gibbsite and bayerite (represented by $Al_2O_3 \cdot 3H_2O$, respectively), boehmite and diaspore (represented by $Al_2O_3 \cdot H_2O$, respectively) and the like.

Among these aluminum oxide compounds, hydrated aluminas are preferred in view of abrasiveness, tooth abrasion and the like. Alumina trihydrates having the formula:

$$Al_2O_3 \cdot 3H_2O \text{ or } Al(OH)_3 \qquad (2)$$

are most preferred because of their mild abrasiveness. The preferred alumina trihydrate is gibbsite which is commercially available.

The aluminum oxide compounds may be used alone or in admixture of two or more.

In view of tooth cleaning and abrasing effects, the aluminum oxide compound should be in the form of particles having an average particle size of 1–50 microns, preferably 3–25 microns when measured by the sedimentation method. The aluminum oxide compound is blended in an amount of 20–90% by weight, preferably 30–60% by weight of a dentifrice composition although the exact blending amount may vary with a particular type of the dentifrice composition.

In addition to the aluminum oxide compound incorporated as the main abrasive as mentioned above, the dentifrice composition of this invention may further include other additional abrasives, for example, dicalcium phosphate dihydrate and anhydride, calcium carbonate, calcium pyrophosphate, silica, aluminum silicate, insoluble sodium metaphosphate, magnesium tertiary phosphate, magnesium carbonate, synthetic resins and other known abrasives alone or in admixture in such amounts that they do not adversely affect the stability of both dextranase and the dentifrice composition (the amount being usually less than 10% by weight of the aluminum oxide main abrasive).

In addition to dextranase, the dentifrice composition of this invention may further include other additional active ingredients, for example, enzymes such as amylase, protease, mutanase, lysozyme, lytic enzyme, etc., alkali metal monofluorophosphates such as sodium monofluorophosphate and potassium monofluorophosphate, fluorides such as sodium fluoride, stannous fluoride, etc., chlorohexidine salts, $\epsilon$-aminocaproic acid, tranexamic acid, aluminum chlorohydroxyallantoinate, dihydrocholesterol, glycyrrhetinates, glycerophosphate, sodium chloride, water-soluble inorganic phosphates, and the like alone or in admixture. Preferably alkali metal monofluorophosphates such as sodium monofluorophosphate may be combined with dextranase because they not only stabilize dextranase, but also retain sufficient dextranase in aged dentifrice compositions. In this case, the content of alkali metal monofluorophosphates may preferably be in the range of 0.1–1% by weight. Mutanase coacts with dextranase to provide a synergistic effect of dissolving dental plaque and preventing reformation of dental plaque. Dextranase may advantageously be combined with lytic enzyme to increase the efficacy thereof. Examples of the water-soluble inorganic phosphate are potassium and sodium salts of orthophosphoric acid, pyrophosphoric acid and polyphosphoric acid, while the potassium salts are preferred.

The dentifrice composition of this invention may further include other well-known ingredients depending on a particular type of the composition.

In the case of toothpastes, a binder may be blended generally in an amount of 0.3–5% by weight, including carrageenan, cellulose derivatives such as sodium carboxymethyl cellulose, alkali metal alginates such as sodium alginate, gums such as veegum and xanthan gum, synthetic binding agents such as polyvinyl alcohol, inorganic binding agents such as silica gel, aluminum silicate gel, etc. and mixtures thereof. Particularly when an alkali metal monofluorophosphate is used as an additional active ingredient, carrageenan and alkali metal alginates may preferably be incorporated to improve the stability and the feeling of toothpastes. Particularly toothpastes containing kappa-carrageenan are stable and advantageous because kappa-carrageenan is more effective to smooth the toothpaste surface than usually available kappa-/iota-carrageenan mixtures.

A humectant may also be blended generally in an amount of 10–70% by weight, including sorbitol, glycerine, ethylene glycol, propylene glycol, 1,3-butylene glycol, polyethylene glycol, xylitol, maltitol, lactitol, etc. and mixtures thereof. Preferably 1–5% by weight of propylene glycol may be used as a binder disperser. Although larger amounts of propylene glycol used tend to reduce the retentivity of dextranase in an aged composition, a humectant mixture of 1 part by weight of propylene glycol and 6–60 parts by weight of sorbitol is free of such tendency.

Also included are anionic surfactants such as water-soluble salts of the higher alkyl sulfates having 8 to 18 carbon atoms in the alkyl group (e.g., sodium lauryl sulfate and sodium mirystyl sulfate), water-soluble salts of sulfonated monoglycerides of higher fatty acids having 10 to 18 carbon atoms in the fatty acid group (e.g. sodium lauryl monoglyceride sulfonate and sodium coconut monoglyceride sulfonate), salts of amides of higher fatty acid having 12 to 16 carbon atoms in the fatty acid group with lower aliphatic amino acids (e.g. sodium-N-methyl-N-palmitoyl touride, sodium N-lauroyl sarcosinate and sodium N-lauroyl-β-alanine); nonionic surfactants such as alkyrol diethanol amides (e.g. lauroyl diethanol amide), stearyl monoglyceride, sucrose fatty acid esters having 12 to 18 carbon atoms in the fatty acid group (e.g. sucrose monolaurate and dilaurate), lactose fatty acid esters, lactitol fatty acid esters, maltitol fatty acid esters, condensates of sorbitan monostearate with approximately 60 moles of ethylene oxide, condensates of ethylene oxide with propylene oxide condensates of propylene glycol and their derivatives (e.g. polyoxyethylene polyoxypropylene monolauryl ester), etc.; amphoteric surfactants such as those of betaine and amino acid types, etc., alone or in admixture in an amount of 0.5–7% by weight; a flavor, for example, essential oils such as peppermint, spearmint, etc., and isolated or synthetic flavor materials such as l-menthol, carvone, eugenol, anethole, etc. alone or in admixture in an amount of 0.1–5% by weight; a sweetener such as sodium saccharin, stevioside, neohesperidin dihydrocalcone, glycyrrhizin, perillartine, p-methoxycinnamic aldehyde, etc.; a preservative such as p-hydroxy methyl benzoic acid, p-hydroxy-butyl benzoic acid, etc.; and other ingredients. Toothpastes may be prepared by kneading the desired ingredients selected from the foregoing ingredients with a proper amount of water.

The toothpaste composition according to this invention may generally have a pH of 4.5 to 10, preferably 6 to 8.5.

The thus prepared dentifrice composition may be ready for use only after it is packed in a suitable container, for example, aluminum tubes, laminate tubes having an aluminum foil laminated with a plastic lamina on either side, plastic tubes, bottles, aerosol containers or the like.

The following examples are illustrative of this invention. However, it is to be understood that the invention is not limited to the Examples. All percents are by weight.

EXAMPLE 1

A toothpaste containing a hydrated alumina as an abrasive (the invention) and another toothpaste containing dicalcium phosphate dihydrate as an abrasive (control) were prepared using the following formulations.

|  | Invention (%) | Control (%) |
| --- | --- | --- |
| Hydrated alumina (gibbsite $Al_2O_3.3H_2O$, average particle size 9 microns) | 50 | — |
| Dicalcium phosphate dihydrate | — | 50 |
| Sorbitol | 20 | 20 |
| Sodium lauryl sulfate | 1.5 | 1.5 |
| Lauroyl diethanol amide | 1.5 | 1.5 |
| Kappa-carrageenan | 0.3 | 0.3 |
| Sodium alginate | 0.7 | 0.7 |
| Gelatin | 0.5 | 0.5 |
| Sodium saccharin | 0.15 | 0.15 |
| Flavor | 1.0 | 1.0 |
| Sodium monofluorophosphate | 0.76 | 0.76 |
| Dextranase | 2000 U/g* | 2000 U/g |
| Water | Balance | Balance |
|  | 100.0% | 100.0% |

*U/g = units per gram of toothpaste

After these toothpastes were stored in the room (25°–44° C.) for 45 days, the quantity of remaining dextranase was measured to determine the retentivity of dextranase. A visual observation was made on the appearance of these toothpastes to determine the degree of discoloration for the evaluation of toothpaste stability. The fresh toothpastes were both white. The results are shown below.

|  | Invention | Control |
|---|---|---|
| Dextranase retentivity after 45 days storage | 94% | 81% |
| Dentifrice stability after 45 days storage (discoloration) | No discoloration | Turned yellow |

Similar results were obtained when the hydrated alumina was replaced by alpha-alumina.

It is apparent from the above results that the dentifrice of this invention retains more dextranase and is more stable as compared with the control. These results prove that the aluminum oxide compounds not only increase the stability of dextranase in a dentifrice composition, but also increase the stability of the dentifrice composition itself.

No substantial difference was observed between the present dentifrice and the control with respect to syneresis and other factors.

EXAMPLE 2

Toothpaste

| | |
|---|---|
| Hydrated alumina (gibbsite, average particle size 5 microns) | 45% |
| Fumed silica | 3% |
| Sorbitol | 20% |
| Sodium lauryl sulfate | 1.5% |
| Lauroyl diethanol amide | 0.5% |
| Carrageenan | 1.0% |
| Sodium saccharin | 0.1% |
| Flavor | 1.0% |
| Dextranase | 3000 U/g |
| Water | Balance |
| | 100.0% |

EXAMPLE 3

Toothpaste

| | |
|---|---|
| Hydrated alumina ($Al_2O_3.3H_2O$, average particle size 15 microns) | 50% |
| Propylene glycol | 2% |
| Sorbitol | 25% |
| Sodium lauryl sulfate | 1.0% |
| Sucrose coconut oil fatty acid ester (D.S. = 1.2) | 2.0% |
| Sodium alginate | 0.5% |
| Kappa-carrageenan | 0.5% |
| Sodium saccharin | 0.1% |
| Sodium monofluorophosphate | 0.76% |
| Flavor | 1.0% |
| Dextranase | 1000 U/g |
| Water | Balance |
| | 100.0% |

EXAMPLE 4

Toothpaste

| | |
|---|---|
| Hydrated alumina (gibbsite, average particle size 10 microns) | 50% |
| Sorbitol | 15% |
| Glycerin | 10% |
| Alpha-olefin sulfonate | 2.0% |
| Lauroyl diethanol amide | 1.0% |
| Gelatin | 0.2% |
| Sodium carboxymethyl cellulose | 1.0% |
| Sodium saccharin | 0.1% |
| Flavor | 1.0% |
| Dextranase | 2500 U/g |
| Chlorohexidine hydrochloride | 0.01% |
| Water | Balance |
| | 100.0% |

EXAMPLE 5

Toothpaste

| | |
|---|---|
| Hydrated alumina (boehmite $Al_2O_3.H_2O$, average particle size 10 microns) | 40% |
| Sorbitol | 20% |
| Sodium lauryl sulfate | 1.0% |
| Kappa-carrageenan | 0.3% |
| Sodium alginate | 0.7% |
| Sodium saccharin | 0.1% |
| Flavor | 1.0% |
| Sodium monofluorophosphate | 0.76% |
| Dextranase | 10,000 U/g |
| Water | Balance |
| | 100.0% |

EXAMPLE 6

Toothpaste

| | |
|---|---|
| Hydrated alumina (gibbsite, average particle size 20 microns) | 40% |
| Calcium pyrophosphate | 4% |
| Glycerin | 20% |
| Sodium lauryl sulfate | 0.7% |
| Sodium N—lauroyl sarcosinate | 0.5% |
| Lauroyl diethanol amide | 2.0% |
| Sodium alginate | 1.0% |
| Sodium saccharin | 0.2% |
| Peppermint oil | 1.0% |
| Dipotassium phosphate | 0.3% |
| Dextranase | 5000 U/g |
| Water | Balance |
| | 100.0% |

EXAMPLE 7

Toothpaste

| | |
|---|---|
| Alpha-alumina (average particle size 5 microns) | 50% |
| Sorbitol | 15% |
| Lactitol hardened tarrow fatty acid ester (D.S. = 1.1) | 2.0% |
| Carrageenan | 1.0% |
| Sodium saccharin | 0.1% |
| Flavor | 1.0% |
| Dextranase | 20,000 U/g |
| Tranexamic acid | 0.1% |
| Water | Balance |
| | 100.0% |

EXAMPLE 8

Toothpowder

| | |
|---|---|
| Hydrated alumina (gibbsite, average particle size 3 microns) | 80% |
| Glycerin | 10% |

| | |
|---|---|
| Sodium lauryl sulfate | 0.1% |
| Sodium saccharin | 0.1% |
| Spearmint oil | 1.0% |
| Dextranase | 2000 U/g |
| Water | Balance |
| | 100.0% |

The dentifrices of Examples 2-8 were found to be highly stable as such and dextranase was retained in a stable manner.

What is claimed is:

1. A dentifrice composition, consisting essentially of: 100-100,000 units of dextranase per gram of the composition; and an aluminum oxide compound having the formula:

$$Al_2O_3 \cdot nH_2O$$

wherein $n \geq 0$, with an average particle size of 1 to 50 microns incorporated as a main abrasive in an amount of 20 to 90% by weight of the composition wherein the activity of the dextranase is stable upon storage.

2. A dextranase containing dentifrice composition having improved dextranase stability, consisting essentially of:
100-100,000 units of dextranase per gram of the composition and 20-90% by weight of the composition of an aluminum oxide trihydrate having the formula:

$$Al_2O_3 \cdot 3H_2O$$

having an average particle size of 1 to 50 microns, said aluminum oxide trihydrate being present as a main abrasive and additional abrasives being present in an amount less than 10% by weight of the aluminum oxide trihydrate main abrasive, thereby maintaining the stability of the dextranase in the composition.

3. A dentifrice composition according to claim 2, wherein the aluminum oxide trihydrate is gibbsite.

4. A dentifrice composition according to claim 2, and further including an alkali metal monofluorophosphate.

5. A dentifrice composition according to claim 2, having a pH of 4.5 to 10.

6. A dentifrice composition according to claim 2, having a pH of 6 to 8.5.

7. A dentifrice composition according to claim 2, wherein said aluminum oxide trihydrate is present in an amount of 30-60% by weight of the composition.

8. A dentifrice composition according to claim 2, wherein said average particle size is 3-25 microns.

9. A dentifrice composition according to claim 2, wherein a binder is present in the composition in an amount of 0.3-5% by weight.

10. A dentifrice composition according to claim 2, wherein an alkali metal monofluorophosphate is present in an amount of 0.1 to 1% by weight.

11. A dentifrice composition according to claim 2, wherein a humectant is present in an amount of 10-70% by weight.

12. A dentifrice composition according to claim 2, wherein a nonionic surfactant is present in an amount of 0.5-7% by weight.

13. A dentifrice composition according to claim 2, wherein an alkali metal monofluorophosphate is present in an amount of 0.1-1% by weight and a nonionic surfactant is present in an amount of 0.5-7% by weight.

14. A dentifrice composition according to claim 12 or 13, wherein the nonionic surfactant is selected from the group consisting of an alkylol diethanol amide, stearyl monoglyceride, a sucrose fatty acid ester, a lactose fatty acid ester, a lactitol fatty acid ester, a maltitol fatty acid ester, a condensate of sorbitan monostearate with approximately 60 moles of ethylene oxide, a condensate of ethylene oxide with propylene oxide, condensates of propylene glycol and their derivatives and mixtures thereof.

15. A dentifrice composition according to claim 12 or 13, wherein the nonionic surfactant is selected from the group consisting of lauroyl diethanol amide, a sucrose fatty acid ester having 12 to 18 carbon atoms in the fatty acid group and mixtures thereof.

* * * * *